(12) United States Patent    (10) Patent No.: US 9,161,588 B2
Chen    (45) Date of Patent: Oct. 20, 2015

(54) ADJUSTABLE HEADBAND DEVICE FOR A HELMET

(71) Applicant: MINSON ENTERPRISES CO., LTD., Taipei (TW)

(72) Inventor: Tai-Heng Chen, Taipei (TW)

(73) Assignee: MINSON ENTERPRISES CO., LTD., Taipei (TW)

( * ) Notice: Subject to any disclaimer, the term of this patent is extended or adjusted under 35 U.S.C. 154(b) by 187 days.

(21) Appl. No.: 14/058,693

(22) Filed: Oct. 21, 2013

(65) Prior Publication Data

US 2015/0107006 A1    Apr. 23, 2015

(51) Int. Cl.
   *A42B 1/22*      (2006.01)
   *A42B 3/32*      (2006.01)
   *A61F 9/02*      (2006.01)

(52) U.S. Cl.
   CPC *A42B 3/324* (2013.01); *A61F 9/027* (2013.01)

(58) Field of Classification Search
   CPC ................................. A42B 3/324; A61F 9/027
   USPC .................................................. 2/417–419, 9
   See application file for complete search history.

(56) References Cited

U.S. PATENT DOCUMENTS

| 2,205,742 | A | * | 6/1940 | Bowers | 2/8.1 |
| 2,926,406 | A | * | 3/1960 | Edwards et al. | 24/68 B |
| 3,214,809 | A | * | 11/1965 | Edwards | 24/68 B |
| 5,357,654 | A | * | 10/1994 | Hsing-Chi | 24/68 B |
| 6,314,588 | B1 | * | 11/2001 | Fang | 2/418 |
| 6,332,227 | B1 | * | 12/2001 | Fang | 2/418 |
| 6,708,376 | B1 | * | 3/2004 | Landry | 24/68 R |
| 7,000,262 | B2 | * | 2/2006 | Bielefeld | 2/418 |
| 7,043,772 | B2 | * | 5/2006 | Bielefeld et al. | 2/418 |
| 7,174,575 | B1 | * | 2/2007 | Scherer | 2/418 |
| 7,222,374 | B2 | * | 5/2007 | Musal et al. | 2/421 |
| 7,441,282 | B2 | * | 10/2008 | Heine et al. | 2/418 |
| 7,707,695 | B2 | * | 5/2010 | Dubois | 24/68 B |
| 8,032,993 | B2 | * | 10/2011 | Musal | 24/68 B |
| 8,206,327 | B2 | * | 6/2012 | Wu | 601/46 |
| 8,359,672 | B2 | * | 1/2013 | Moelker | 2/418 |
| 8,434,200 | B2 | * | 5/2013 | Chen | 24/68 SK |
| 2006/0015988 | A1 | * | 1/2006 | Philpott et al. | 2/410 |
| 2007/0079429 | A1 | * | 4/2007 | Pilon et al. | 2/410 |
| 2007/0266481 | A1 | * | 11/2007 | Alexander et al. | 2/414 |
| 2008/0092279 | A1 | * | 4/2008 | Chiang | 2/425 |
| 2008/0189835 | A1 | * | 8/2008 | Mangone | 2/420 |
| 2008/0276354 | A1 | * | 11/2008 | Stokes et al. | 2/418 |
| 2008/0295229 | A1 | * | 12/2008 | Fang | 2/418 |
| 2009/0031482 | A1 | * | 2/2009 | Stokes et al. | 2/414 |
| 2009/0320187 | A1 | * | 12/2009 | Petzl et al. | 2/417 |
| 2010/0050325 | A1 | * | 3/2010 | Wang-Lee | 2/418 |
| 2011/0088148 | A1 | * | 4/2011 | Chen | 2/418 |
| 2011/0167543 | A1 | * | 7/2011 | Kovacevich et al. | 2/417 |
| 2011/0191946 | A1 | * | 8/2011 | Fang | 2/418 |
| 2012/0296245 | A1 | * | 11/2012 | Ma et al. | 601/84 |
| 2013/0139304 | A1 | * | 6/2013 | Moelker | 2/418 |
| 2015/0059065 | A1 | * | 3/2015 | Klotz et al. | 2/418 |

\* cited by examiner

*Primary Examiner* — Khoa Huynh
*Assistant Examiner* — Jocelyn Wu
(74) *Attorney, Agent, or Firm* — WPAT, P.C.; Anthony King (57) ABSTRACT

An adjustable headband device for a helmet has a base, a headband, a driven wheel, a resilient element, a cover plate and an adjusting knob. The headband is mounted on the base and has two toothed racks. The driven wheel has a gear engaging the toothed racks, multiple engaging tabs and multiple ratchet pawls. The cover plate is mounted on the base and has multiple ratchet teeth selectively engaging the ratchet pawls. The adjusting knob of the adjustable headband device rotates to control increase and decrease of an inner diameter defined by the looped headband without being depressed.

5 Claims, 8 Drawing Sheets

ADJUSTABLE HEADBAND DEVICE FOR A HELMET

BACKGROUND OF THE INVENTION

1. Field of the Invention

The present invention relates to a headband device, and more particularly to an adjustable headband device for a helmet that allows a user to easily adjust a headband for fitting the user's head circumference.

2. Description of Related Art

Helmets are widely used in fields of construction, motorcycling and extreme sports and is worn on a user's head for cushioning external impact on the user's head, thus to provide additional protection to the user's head.

A conventional helmet has a housing, a cushion element and a chin strap. The housing is hard and hollow. The cushion element is mounted in the housing. The chin strap is attached on opposite sides of an opening of the housing and may be tightened on a user's chin to secure the helmet on the user's head. The hard housing and the cushion element cooperate to cushion external impact. However, a size of the helmet cannot be adjusted such that the helmet may be loosely worn on and even fall off from a user' head when the size of the helmet is larger than that of the user's head. Therefore, helmet manufacturers usually produce helmets of different sizes for different users and each user needs to try different sizes of the standardized helmet, which is inconvenient and inefficient for both the manufacturers and users.

A helmet with an adjustable headband has been developed and has the adjustable headband mounted on an inner surface of the helmet. The adjustable headband has two toothed racks formed on two ends of the headband and engaging a gear located therebetween. An adjusting knob is connected to and rotates the gear to drive the toothed racks toward or away from each other, which changes an inner diameter defined by the headband looped into a circle.

To prevent a user from unintentionally increasing the inner diameter of the looped headband due to unexpected vibration or external force, a ratchet wheel and a ratchet pawl are mounted in the adjusting knob to limit the adjusting knob to only rotate in a single rotational direction that allows reducing the inner diameter of the looped headband. To increase the inner diameter of the looped headband, the adjusting knob is pushed to disengage the ratchet wheel from the ratchet pawl, and then the adjusting knob can be rotated reversely to enlarge the inner diameter of the looped headband. After the adjusting knob is released, a biasing spring pushes the adjusting knob back to its original position to re-engage the ratchet wheel with the ratchet pawl.

However, in order to enlarge the inner diameter of the looped headband of the aforementioned helmet with the adjustable headband, the user needs to simultaneously push and rotate the adjusting knob, which is inconvenient.

To overcome the shortcomings, the present invention provides an adjustable headband device for a helmet to mitigate or obviate the aforementioned problems.

SUMMARY OF THE INVENTION

The main objective of the invention is to provide an adjustable headband device for a helmet that allows a user to easily adjust a headband for fitting the user's head circumference.

An adjustable headband device for a helmet in accordance with the present invention has a base, a headband, a driven wheel, a resilient element, a cover plate and an adjusting knob. The headband is mounted on the base and has two toothed racks. The driven wheel has a gear engaging the toothed racks, multiple engaging tabs and multiple ratchet pawls. The cover plate is mounted on the base and has multiple ratchet teeth selectively engaging the ratchet pawls. The adjusting knob of the adjustable headband device rotates to control increase and decrease of an inner diameter defined by the looped headband without being depressed, which is convenient.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
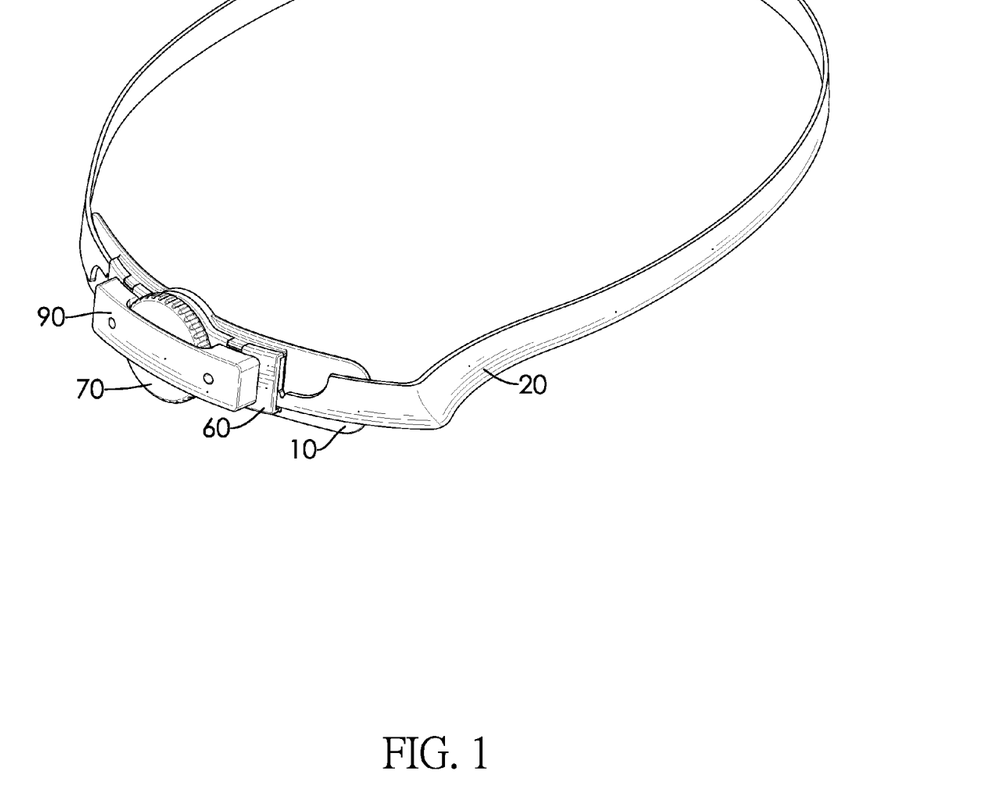
FIG. 1 is a perspective view of an adjustable headband device for a helmet in accordance with the present invention.
Figure 2:
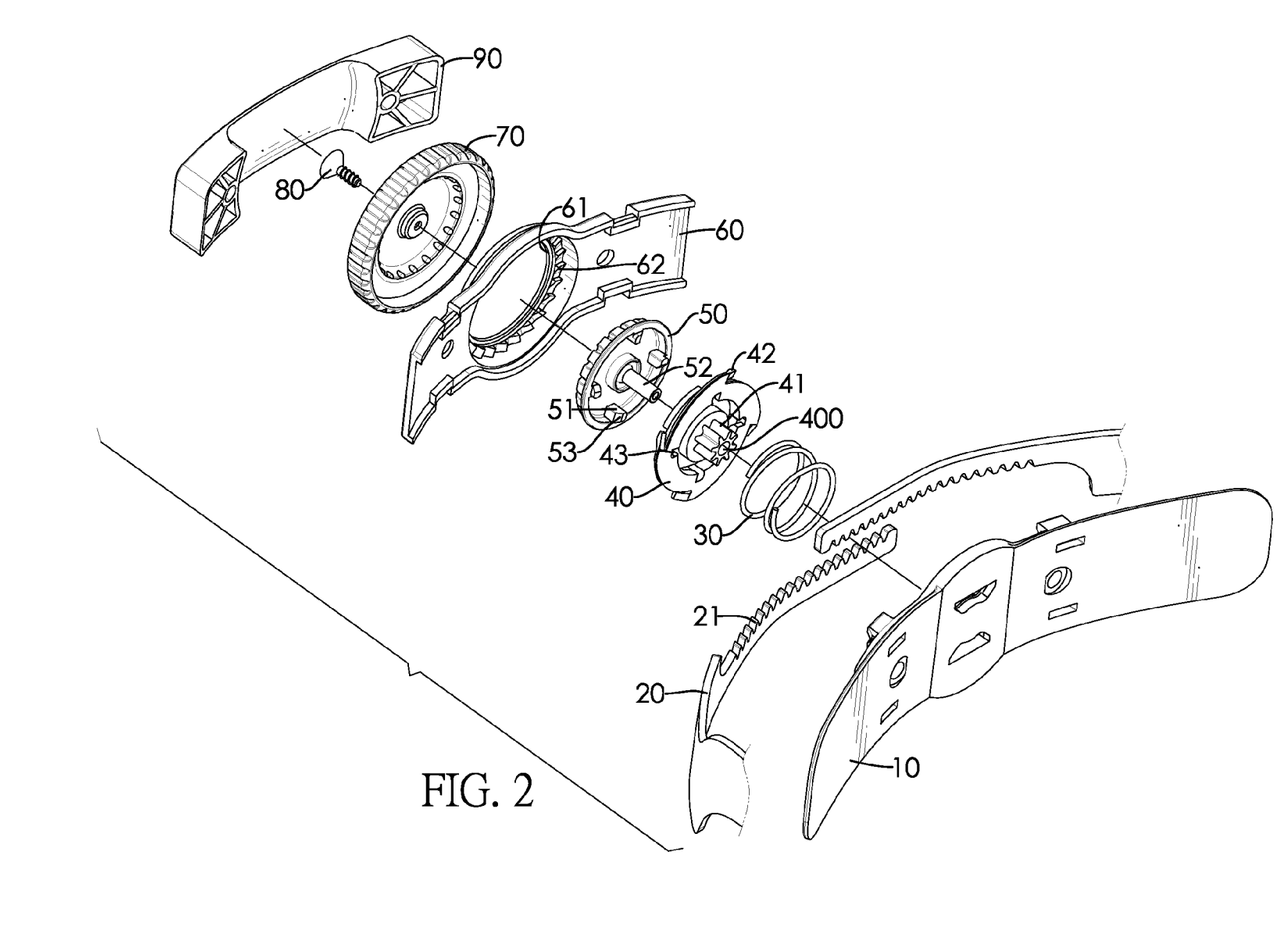
FIG. 2 is a perspective view of the adjustable headband device in FIG. 1.
Figure 3:
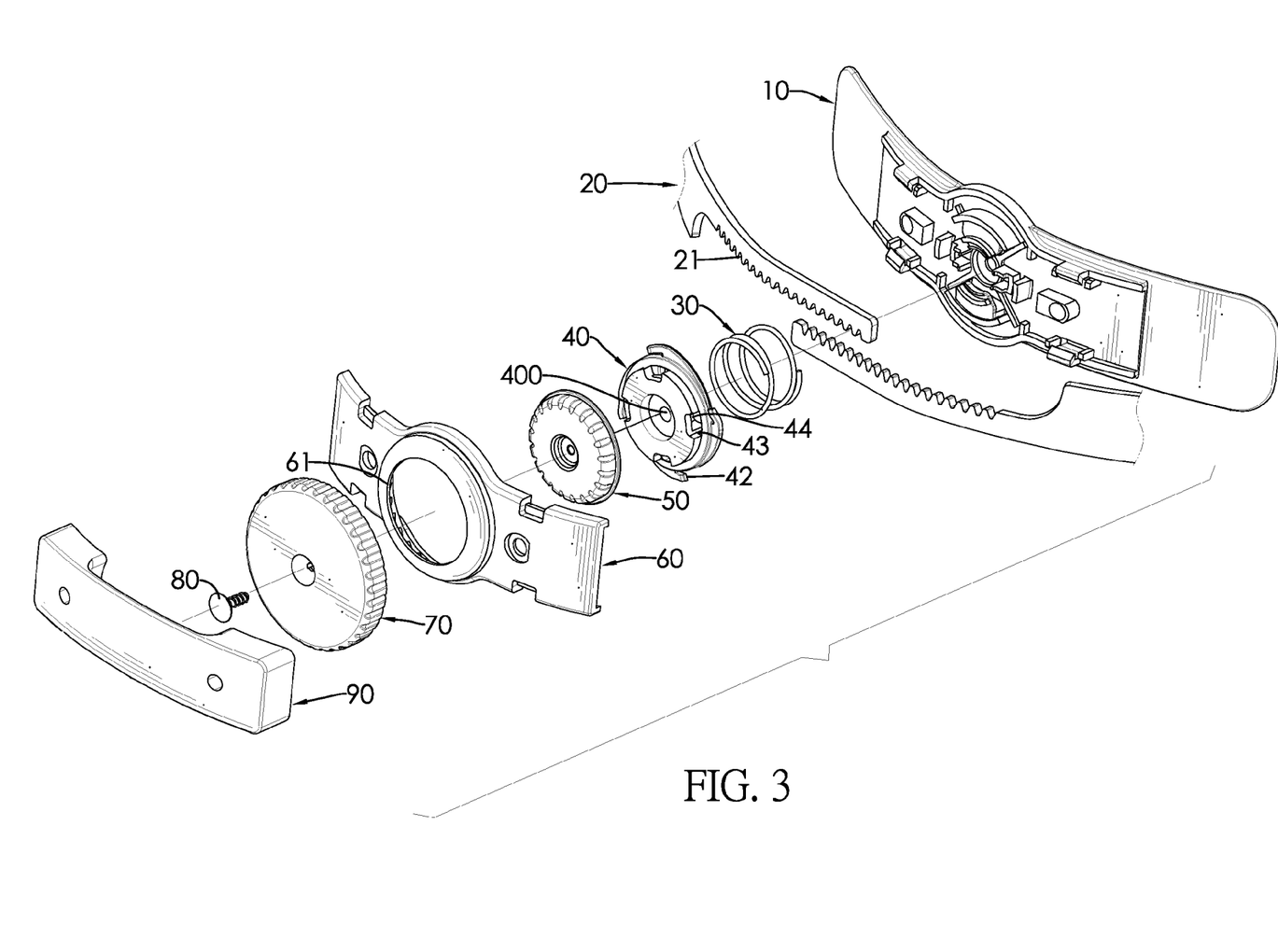
FIG. 3 is another perspective view of the adjustable headband device in FIG. 1.

With reference to FIGS. 1 to 3, an adjustable headband device for a helmet in accordance with the present invention may be mounted securely in an internal space of a helmet and comprises a base 10, a headband 20, a driven wheel 40, a resilient element 30, a cover plate 60, an adjusting knob and a faceplate 90.

The base 10 is elongated.

The headband 20 is an elongated strip, is mounted slidably on the base 10 and has two ends and two toothed racks 21 formed respectively on the ends. Each toothed rack 21 has a set of multiple teeth and the two sets of the teeth face each other.

Figure 4:
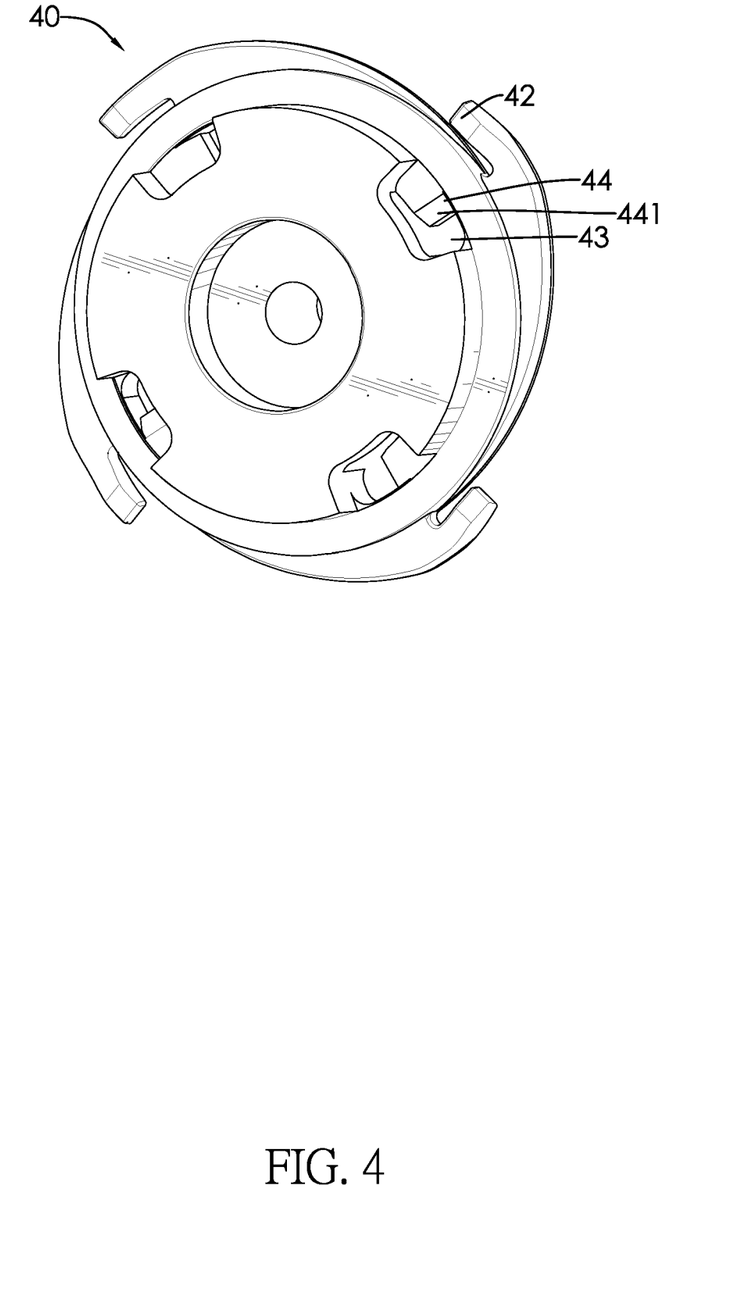
FIG. 4 is an enlarged perspective of a driven wheel of the adjustable headband device in FIG. 2.

With reference to FIGS. 2 to 4, the driven wheel 40 is connected to the headband 20 and has a mounting hole 400, a gear 41, multiple engaging holes 43 and multiple ratchet pawls 42.

The mounting hole 400 is defined axially through the driven wheel 40.

The gear 41 is formed on an inner surface of the driven wheel 40 and engages the toothed racks 21.

The engaging holes 43 are defined through the driven wheel 40 and are arranged in a circle that surrounds the gear 41. Each engaging hole 43 has an abutment tab 44 formed in the engaging hole 43 and having an inclined surface 441.

The ratchet pawls 42 are formed on and protrude radially outward from the driven wheel 40.

The resilient element 30 may be a spring and is mounted between the base 10 and the inner surface of the driven wheel 40.

The cover plate 60 is mounted securely on the base 10, holds the driven wheel 40 between the base 10 and the cover plate 60, and has a central hole 61 and multiple ratchet teeth 62.

The central hole 61 is defined through the cover plate 60.

The ratchet teeth 62 are formed on the cover plate 60, are arranged in a circle that surrounds the central hole 61, and selectively engage the ratchet pawls 42 of the driven wheel 42 respectively.

The adjusting knob is mounted on an outer surface of the driven wheel 40, is mounted rotatably in the central hole 61 of the cover plate 60, and has a shaft 52 and multiple abutment protrusions 51.

The shaft 52 is formed on and protrudes axially from an inner surface of the adjusting knob and is mounted slidably and rotatably in the mounting hole 400 of the driven wheel 40.

The abutment protrusions 51 are formed on and protrude from the inner surface of the adjusting knob, are arranged circularly, are mounted respectively in the engaging holes 43, and selectively slide obliquely on the abutment tabs 44. Each abutment protrusion 51 has an inclined surface 53 facing the inclined surface 441 of the abutment tab 44 of a corresponding engaging hole 43.

In a preferred embodiment, the adjusting knob is assembled from an inside knob member 50 and an outside knob member 70. The inside knob member 50 is mounted rotatably between the driven wheel 40 and the cover plate 60. The outside knob member 70 is mounted securely on the inside knob member 50 and located outside the cover plate 60. The shaft 52 and the abutment protrusions 51 are formed on an inner surface of the inside knob member 50. A fastener 80 such as a bolt is inserted through and holds the inside knob member 50 and the outside knob member 70 together.

The faceplate 90 is mounted securely on the cover plate 60 and covers the outside knob member 70 of the adjusting knob.

Figure 5:
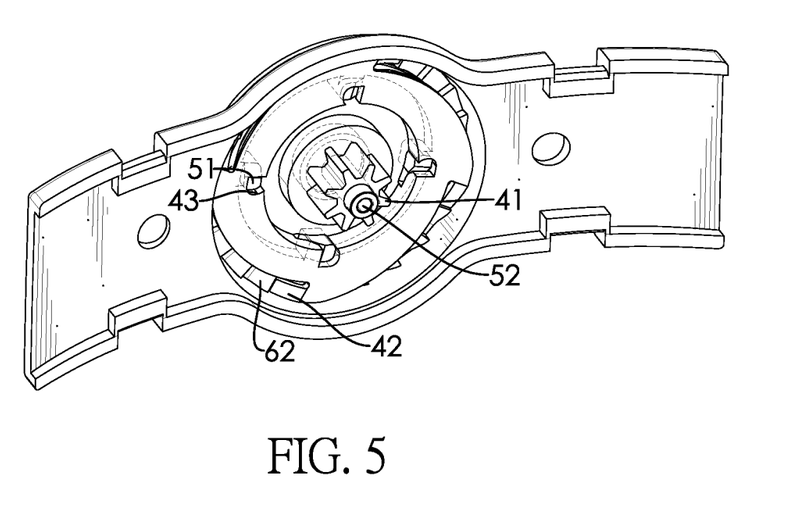
FIG. 5 is an enlarged perspective view of the driven wheel, the adjustable knob and the cover plate of the adjustable headband device in FIG. 2.
Figure 6:
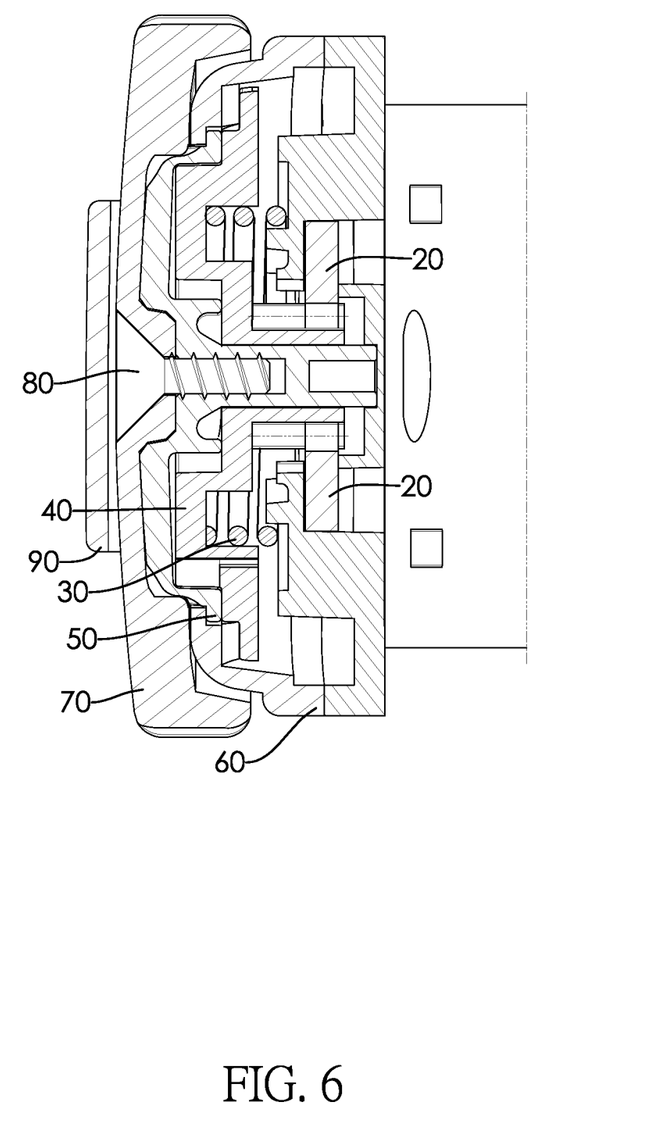
FIG. 6 is a cross sectional side view of the adjustable headband device in FIG. 5.

With reference to FIGS. 5 and 6, to reduce an inner diameter defined by the headband 20 looped into a circle, the adjusting knob is rotated clockwise. The driven wheel 40 is driven by the adjusting knob to rotate clockwise. In the mean time, the ratchet pawls 42 are disengaged respectively from the ratchet teeth 62 so that the driven wheel 40 rotates freely relative to the cover plate 60. The gear 41 of the driven wheel 40 rotates clockwise to drive the toothed racks 21 to move toward each other. Therefore, the inner diameter of the looped headband 20 is reduced.

When the adjusting knob is not manipulated and a user or an unexpected force such as vibration inadvertently pulls the headband 20, the toothed racks 21 tend to move away from each other, but the ratchet pawls 42 of the driven wheel 40 respectively engage the ratchet teeth 62 of the cover plate 60, which prevents the toothed racks 21 from moving. Therefore, the inner diameter of the looped headband 20 is kept from increasing.

Figure 7:
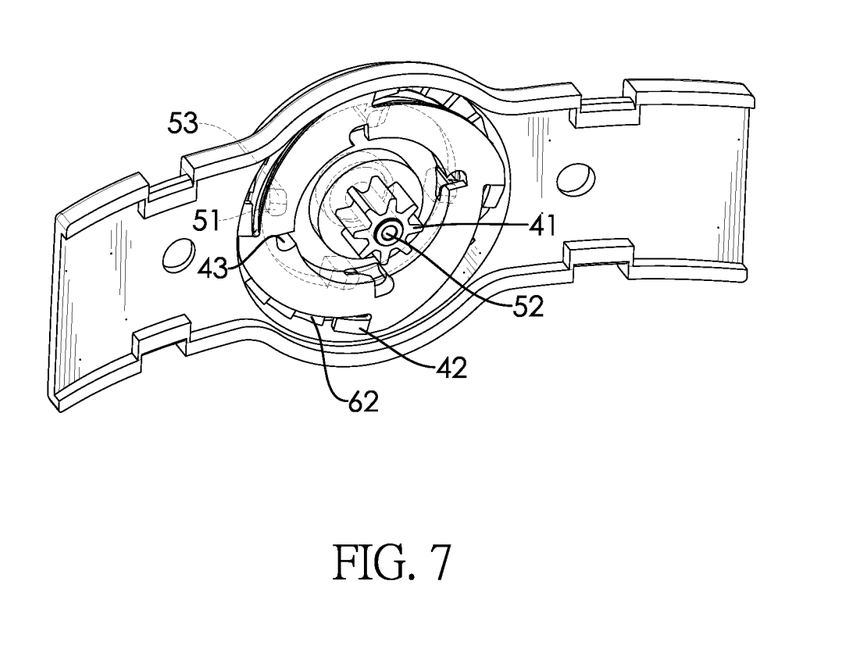
FIG. 7 is an operational enlarged perspective view of the driven wheel, the adjustable knob and the cover plate of the adjustable headband device in FIG. 5.
Figure 8:
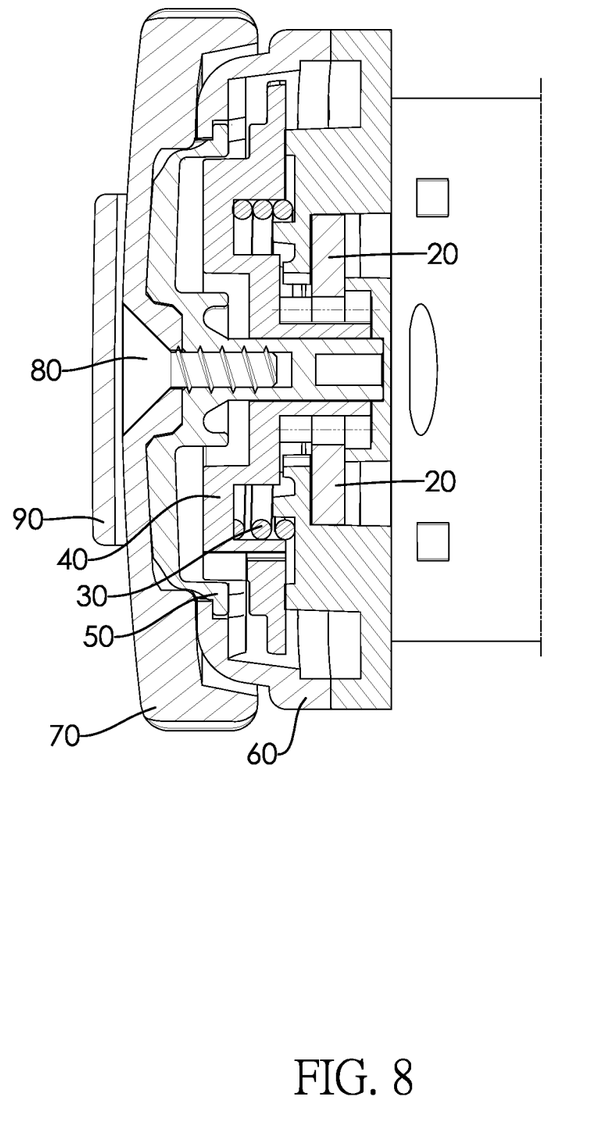
FIG. 8 is a cross sectional side view of the adjustable headband device in FIG. 7.

With reference to FIGS. 7 and 8, to increase the inner diameter of the looped headband 20, the adjusting knob is rotated counterclockwise. The inclined surfaces 53 of the abutment protrusions 51 of the adjusting knob slide relative to the inclined surfaces 441 of the abutment tabs 44 of the driven wheel 40 so that the abutment protrusions 51 move slightly away from the abutment tabs 44. The abutment protrusions 51 of the adjusting knob also push the driven wheel 40 backward relative to the cover plate 60 to disengage the ratchet pawls 42 from the ratchet teeth 62 and compress the resilient element 30. Therefore, the adjusting knob and the driven wheel 40 are synchronously rotated counterclockwise to move the toothed racks 21 away from each other, and the inner diameter of the looped headband 20 is increased.

When the rotating adjusting knob is stopped, the resilient element 30 presses against and moves the driven wheel 40 toward the cover plate 60 and re-engages the ratchet pawls 42 of the driven wheel 40 with the ratchet teeth 62 of the cover plate 60.

The adjustable headband device allows rotating the adjusting knob to control increase and reduction of the inner diameter of the looped headband 20 for different users' head circumferences without simultaneously pushing the adjusting knob, so that the manipulation of the adjusting knob is easy and convenient. Furthermore, the engaging ratchet pawls 42 and the ratchet teeth 62 prevent the user or unexpected force from inadvertently pulling the headband 20 and increasing the inner diameter of the looped headband 20.

Even though numerous characteristics and advantages of the present invention have been set forth in the foregoing description, together with details of the structure and function of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An adjustable headband device for a helmet comprising:
   a base;
   a headband mounted slidably on the base and having two toothed racks formed respectively on two ends of the headband;
   a driven wheel connected to the headband and having
      a mounting hole defined axially through the driven wheel;
      a gear formed on an inner surface of the driven wheel and engaging the toothed racks;
      multiple engaging holes defined through the driven wheel and arranged in a circle that surrounds the gear, and each engaging hole having an abutment tab formed in the engaging hole and having an inclined surface; and
      multiple ratchet pawls formed on and protruding radially outward from the driven wheel;
   a resilient element mounted between the base and the inner surface of the driven wheel;
   a cover plate mounted securely on the base, holding the driven wheel between the base, and the cover plate and having
      a central hole defined through the cover plate; and
      multiple ratchet teeth formed on the cover plate, arranged in a circle that surrounds the central hole, and selectively engaging the ratchet pawls of the driven wheel respectively; and
   an adjusting knob mounted on an outer surface of the driven wheel, mounted rotatably in the central hole of the cover plate, and having
      a shaft formed on and protruding axially from an inner surface of the adjusting knob and mounted slidably and rotatably in the mounting hole of the driven wheel; and
      multiple abutment protrusions formed on and protruding from the inner surface of the adjusting knob, mounted respectively in the engaging holes, and selectively sliding obliquely on the abutment tabs.

2. The adjustable headband device as claimed in claim 1, wherein
   the adjusting knob has
      an inside knob member mounted rotatably between the driven wheel and the cover plate; and an outside knob member mounted securely on the inside knob member and located outside the cover plate; and the shaft and the abutment protrusions are formed on an inner surface of the inside knob member.

3. The adjustable headband device as claimed in claim 2, wherein a fastener is inserted through and holds the inside knob member and the outside knob member together.

4. The adjustable headband device as claimed in claim 3, wherein a faceplate is mounted securely on the cover plate and covers the outside knob member of the adjusting knob.

5. The adjustable headband device as claimed in claim 4, wherein the resilient element is a spring.

\* \* \* \* \*